US 008821462B2

(12) United States Patent
Axelsson et al.

(10) Patent No.: US 8,821,462 B2
(45) Date of Patent: Sep. 2, 2014

(54) PERCUTANEOUS ABDOMINAL IMPLANT (75) Inventors: Robert Axelsson, Gränna (SE); Martin Johansson, Valda (SE); Bjørn Edwin, Sætre (NO); Erik Fosse, Oslo (NO)

(73) Assignee: Ostomycure AS, Oslo (NO)

( * ) Notice: Subject to any disclaimer, the term of this patent is extended or adjusted under 35 U.S.C. 154(b) by 708 days.

(21) Appl. No.: 12/674,666

(22) PCT Filed: Aug. 19, 2008

(86) PCT No.: PCT/EP2008/060837
§ 371 (c)(1),
(2), (4) Date: Apr. 11, 2011

(87) PCT Pub. No.: WO2009/024568
PCT Pub. Date: Feb. 26, 2009

(65) Prior Publication Data
US 2011/0178540 A1 Jul. 21, 2011

(30) Foreign Application Priority Data
Aug. 21, 2007 (EP) ..................................... 07114671

(51) Int. Cl.
*A61F 5/44* (2006.01)
*A61M 39/02* (2006.01)
*A61F 5/445* (2006.01)

(52) U.S. Cl.
CPC ............ *A61F 5/445* (2013.01); *A61M 39/0247* (2013.01); *A61M 2039/0261* (2013.01); *A61F 2005/4455* (2013.01)
USPC ...................................................... 604/332

(58) Field of Classification Search
USPC ...................................................... 604/332
See application file for complete search history.

(56) References Cited

U.S. PATENT DOCUMENTS 3,663,965 A * 5/1972 Lee et al. ................... 623/23.64
4,119,100 A 10/1978 Rickett ......................... 128/350

(Continued)

FOREIGN PATENT DOCUMENTS

EP 0 477 475 B1 4/1992
EP 1 632 201 B1 3/2006

(Continued)

OTHER PUBLICATIONS

Machine Translation of description of WO 2005/056079 A1 to Skiera et al. Translated by http://ep.espacenet.com/ on Feb. 23, 2011.

(Continued)

*Primary Examiner* — Susan Su
*Assistant Examiner* — Guy K Townsend
(74) *Attorney, Agent, or Firm* — Winston & Strawn LLP (57) ABSTRACT An implant for percutaneous implantation through the abdominal wall for encircling and engaging an externalized length of a body duct of a human or animal patient. The implant has an exterior tubular section defined by an circumferential exterior wall at least a part of which is adapted to protrude outwardly from the abdominal wall with a free end for mounting of a detachable device, an interior section defined by an circumferential interior wall adapted to extend through the abdominal wall and inside the patient for internal fixation of the implant, wherein the exterior tubular section and the interior section have a common axis A. The circumferential exterior wall of the exterior tubular section and the circumferential interior wall of the interior section are arranged axially spaced apart at a distance D from each other to provide an axial gap between opposing free ends of the exterior tubular section and the interior section, with the exterior tubular section and interior section being connected inside the sections.

21 Claims, 4 Drawing Sheets (56) References Cited

U.S. PATENT DOCUMENTS

| | | | | |
|---|---|---|---|---|
| 4,183,357 | A | | 1/1980 | Bentley et al. ............... 128/283 |
| 4,217,664 | A | | 8/1980 | Faso ..................................... 3/1 |
| 5,098,397 | A | * | 3/1992 | Svensson et al. ............ 604/175 |
| 5,423,761 | A | * | 6/1995 | Hein et al. ............... 604/167.01 |
| 5,425,761 | A | * | 6/1995 | Lundgren ................. 623/11.11 |
| 5,882,341 | A | | 3/1999 | Bousquet ...................... 604/175 |
| 6,017,355 | A | * | 1/2000 | Hessel et al. .................. 606/184 |
| 6,438,397 | B1 | | 8/2002 | Bosquet et al. ............ 600/310 |
| 7,935,096 | B2 | * | 5/2011 | Johansson et al. ............ 604/338 |
| 2001/0051794 | A1 | | 12/2001 | Bestetti et al. .......... 604/288.04 |
| 2002/0099344 | A1 | | 7/2002 | Hessel et al. .................. 604/338 |
| 2004/0006396 | A1 | | 1/2004 | Ricci et al. ...................... 623/32 |
| 2006/0052759 | A1 | * | 3/2006 | Johansson et al. ............ 604/277 |
| 2009/0192464 | A1 | * | 7/2009 | Axelsson et al. ........ 604/164.04 |
| 2011/0178540 | A1 | * | 7/2011 | Axelsson et al. ............. 606/153 |
| 2011/0196324 | A1 | * | 8/2011 | Johansson et al. ............ 604/338 |
| 2012/0123361 | A1 | * | 5/2012 | Johansson et al. ............ 604/337 |

FOREIGN PATENT DOCUMENTS

| | | |
|---|---|---|
| GB | 2 045 084 A | 10/1980 |
| GB | 2 105 197 A | 3/1983 |
| JP | 2002-507901 A | 3/2002 |
| WO | WO 98/58691 A1 | 12/1998 |
| WO | WO 00/62722 A1 | 10/2000 |
| WO | WO 01/08597 A1 | 2/2001 |
| WO | WO 2005/056079 A1 | 6/2005 |
| WO | WO 2007/099500 A1 | 9/2007 |

OTHER PUBLICATIONS

International Search Report and Written Opinion, Appl. No. PCT/IB2007/050646, Jul. 27, 2007.
U.S. Appl. No. 12/280,610, filed Oct. 29, 2008.
U.S. Appl. No. 12/280,610, Restriction Requirement, Dec. 23, 2010.
U.S. Appl. No. 12/280,610, Non-Final Office Action, Mar. 22, 2011.
U.S. Appl. No. 12/280,610, Applicant-Initiated Interview Summary, Sep. 16, 2011.
US Appl. No. 12/280,610, Non-Final Office Action, Mar. 16, 2012.
U.S. Appl. No. 12/280,610, Final Office Action, Jan. 9, 2013.
U.S. Appl. No. 12/280,610, Advisory Action, Mar. 15, 2013.
U.S. Appl. No. 12/280,610, Applicant-Initiated Interview Summary, Apr. 12, 2013.
International Search Report, PCT/EP2008/060837, mailed Nov. 7, 2008.
European Search Report, Application No. 07114671 dated Dec. 4, 2007.

* cited by examiner

PERCUTANEOUS ABDOMINAL IMPLANT

This application is a 371 filing of International Patent Application PCT/EP2008/060837 filed Aug. 19, 2008.

BACKGROUND

The present invention relates to an implant for percutaneous implantation through the abdominal wall for encircling and engaging an externalised length of a body duct of a human or animal patient. The implant is of the kind comprising an exterior tubular section defined by an circumferential exterior wall at least a part of which is adapted to protrude outwardly from the abdominal wall with a free end which serves for mounting of a detachable device, an interior section defined by an circumferential interior wall adapted to extend through the abdominal wall and inside the patient for internal fixation of the implant, wherein the exterior tubular section and the interior section have a common axis.

A detailed discussion of various diseases and known surgical procedures involving ostomy are found in the applicants own European patent application No. EP 0477475.4 and international patent application PCT/IB2007/050646, not yet published.

A tubular implant with a flange is known from U.S. Pat. No. 4,217,664. This implant is used as a permanent, closable stoma and includes a flexible, pliable sleeve of biocompatible, soft, mesh material, e.g. polypropylene. Since a flexible sleeve can move in response to the peristaltic movements of the externalised intestine there is a great risk that the connection of the tissue growing into the sleeve is too weak at the beginning of the healing process to resist peristaltic movement. The fragile tissue bond may rupture in response to movement of the sleeve during peristaltic and in response to passage of substance. This prevents fast healing and protracts patient recovery. In addition due to the required folding technique of the intestine around the free edge of the implant to allow the intestinal tissue to get attached to the flexible mesh, infectious material is guided directly towards the exterior skin surface, inducing a considerable risk of irritation, inflammation and last but not least bacterial contamination with a.o. faecal matter on the surrounding skin surface, in particular during healing.

The applicants own patent applications describes various embodiments of implants provided with rigid mesh means along various parts of the interior circumference of the implant. Although theses implant have proven to be of particular advantage for many ostomy patients it has turned out that in some patient's uncontrollable infection and inflammation occurs, in particular at the contact site between the exterior surface of the implant and the access opening in the abdominal skin of the patient. It is recognised that the reason for this is the design of these known implants, in which the exterior ring section merges directly into the interior section, for example by means of connecting members. This design provides a microbiological access route or wick for i.e. faecal bacteria along the exterior surface of the implant. This exterior surface also provides a propagating surface for bacteria.

The present invention now remedies these disadvantages.

SUMMARY OF THE INVENTION

In a first aspect according to the present invention is provided an implant of the kind mentioned in the opening paragraph, which enables fast ingrowth of an externalised length of a body duct.

In a second aspect according to the present invention is provided an implant of the kind mentioned in the opening paragraph, which can be implanted with a minimum risk of inflammation, infection and necrosis.

The novel and unique features, whereby this is achieved according to the present invention, is the fact that the circumferential exterior wall of the exterior tubular section and the circumferential interior wall of the interior section are arranged axially spaced apart at a distance from each other to provide an axial gap between opposing free ends of the exterior tubular section and the interior section, said exterior tubular section and interior section are connected by means of distance means.

During the surgical implantation procedure an access opening is made at a relevant site through the abdominal wall. The implant is located in the abdominal opening with the exterior section protruding from the patient and the exterior section anchored inside the body.

The body duct, e.g. the colon, is then externalised through the internal diameter of the implant so that the interior section carefully encircles, guides and supports the externalised body duct. The outmost tissue layer, e.g. the serosa or any other exposed layer of the body duct's exterior wall is thereby brought into engaging contact with interior faces of the implant to trigger the gradual ingrowth of tissue, generation of connective tissue and firm integration of body wall, intestine and implant. This position of the externalised body duct inside the implant may initially be secured using appropriate mechanical means, such as sutures or a stent to support the integration process.

Epithelial cells from the skin protect underlying tissue from mechanical injury, harmful chemicals, invading bacteria and from excessive loss of water. The epithelial cells are packed tightly together, with almost no intercellular spaces and only a small amount of intercellular substance. Epithelial tissue, including skin epithelial tissue, is usually separated from the underlying tissue by a thin sheet of connective tissue, the basement membrane, which provides structural support for the epithelium and also binds it to neighbouring structures. The skin epithelial cells and epidermal cells will respond to the injury resulting from the surgical creation of the access opening for the externalised intestine or other body duct and reunite with any exposed available neighbouring structure to try to fill the wound site, i.e. the access opening, and repair the injury.

The exterior surface of the implant and the skin epithelium is however contaminated with microbiological flora, other contaminants or foreign bodies, which can induce infection and/or inflammation if transferred inside the body during repair of the wound site.

The axial gap between the exterior tubular section and the interior section advantageously serves for interrupting the skin epithelial cell-propagating route towards the interior section. Any contaminating and infectious material associated with the skin epithelial cells or at least the exterior face of the exterior tubular section of the implant, is prevented from getting into contact with the interior section inside the body, which contact could provoke entrance of the undesired subject-matter either directly or by encapsulation during healing. The spaced apart exterior tubular and interior sections contribute substantially to or completely prevent formation of a biofilm at the implanted sections of the implant. Furthermore, skin infections, necrosis of skin or body duct, rejection of implant and many other side-effects of considerable annoyance to the patient, such as skin irritation, redness and itchiness is avoided to a greater extent than hitherto known.

In the most preferred embodiment the above-mentioned advantageous effects may be further improved if the distance means comprises a rigid ingrowth mesh, preferably solely is a rigid ingrowth mesh.

It may further be preferred that the rigid ingrowth mesh is shaped as a tubular body having a length of at least the distance between the exterior tubular section and the interior section so that the rigid ingrowth mesh serves at least for keeping the exterior tubular section and the interior tubular section spaced apart in rigid relationship, connected to each other so that their opposing free ends do not touch each other.

Furthermore, any of the exterior tubular section and the interior section is provided with a rigid ingrowth mesh for ingrowth of at least the exterior surface of the body duct wall along at least a part of any of the internal circumference of the exterior tubular section, the interior section or the distance means.

A circumferential radial gap may advantageously be provided between the distance means and the interior faces of any of the exterior tubular section and the interior section to provide sufficient space for any newly developed tissue formed during healing after implantation, which tissue formation is required to create a firm securing of the externalised body duct, for example an intestine, to both implant and abdominal wall.

New tissue will develop initiated by natural healing processes, and in this embodiment the abdominal wall, which has been surgically cut and exposed, can be secured to the body by means of new generated tissue, which penetrates from the abdominal wall through the circumferential wall of interior section. The externalised body duct located inside the body adjacent the abdominal access opening is secured to the implant by means of ingrowth of tissue originating from the body duct, such as serosa, through the distance means, preferably the ingrowth mesh. The new generated tissue originating from the abdominal wall and the new generated tissue originating from the body duct may meet and grow together in the radial gap inside the body, although this is not required for complete securing of the implant. The created new tissue bonds will completely enclose the interior section to further enhance a very strong, safe and reliable tissue anchorage of the implant inside the body. The new tissue originating from the abdominal skin is not able to, or only to a very limited degree able to, develop through the ingrowth mesh. As a result the ingrowth mesh is mostly infiltrated with new tissue originating from the body duct and the interior section with tissue originating from the abdominal wall.

In the embodiment where the ingrowth mesh and the body duct extends in parallel almost to the free end of the exterior tubular section a major part, if not all, of the ingrowth mesh is infiltrated with new tissue originating from the externalised body duct tissue during healing. Thus, new tissue may be created through all the openings of the ingrowth mesh to infiltrate not only the parts of the ingrowth mesh situated inside the exterior tubular section and the interior section, but also the part of the ingrowth mesh extending in the axial gap between the exterior tubular section and the interior section.

Because an interior annular rim section at the free end of the exterior tubular section is left free of ingrowth mesh, new tissue, such as the body duct mucosa, serosa or any other kind of new tissue, are prevented from propagating around the free end of the exterior tubular section, so that this end is left free for easy mounting of a detachable device, such as an ostomy bag.

The exterior face of the exterior tubular section is free of contact with the access opening and remains un-infiltrated with any new tissue. As mentioned above new tissue which originates from the body duct infiltrates the ingrowth mesh inserted in the exterior tubular section and may occupy some of the space of the radial gap, but bacteria from the skin cannot enter this gap due to the closed exterior surface of the protruding part of the exterior tubular section of the implant.

The exterior skin surface serves as a natural barrier against pathological contaminants, infectants and foreign bodies which may induce destructive processes on the living but injured tissue. In particular the skin constitutes a natural barrier to bacteria. The bacteria and other microbiological material cannot get through the abdominal skin surface and reach the tissue, which encapsulates the interior section to thereby cause deep infections. Any such pathological matter is relegated to the inside face op the implant or to the intact lumen of the body duct.

In an alternative embodiment the distance means may be constituted by circumferentially spaced apart assembling members arranged to provide the circumferential gap. What is essential for a suitable shape of an assembling member is that the ribs must have a suitable length to keep opposing free ends of the exterior tubular section and the interior section spaced apart at a defined and permanent suitable distance. The assembling members must also be shaped to provide the radial gap. Such fitting members may for example be shaped as elongated U-shaped or L-shaped thin ribs, where the free ends of the legs of the U's or L's are secured to the exterior tubular section and the interior section, respectively, to provide the radial gap distance, and the bottom of the U or right angle of the L provide the axial gap distance.

In order to obtain a firm internal biological anchor the interior section may advantageously extend into an anchoring flange for anchoring the implant inside the body, said anchoring flange extends radially of the interior section opposite the exterior tubular section.

Tissue ingrowth is expedited if any of the interior section and the anchoring flange comprises a plurality of through-opening of the same or different sizes or combination of sizes to allow infiltration of tissue and creation of a tissue bond.

It has turned out that if the rigid ingrowth mesh has a plurality of passageways, channels or openings, preferably of a polygonal cross-section the infiltration of the ingrowth means is facilitated. It is most preferred that the plurality of passageways, channels or openings are of hexagonal cross-section.

If the plurality of passageways, channels or openings of the rigid ingrowth mesh is made by laser cutting they can be given any appropriate size and shape. Moreover, it is very easy to control and direct the laser beam so that the laser cutting edges of the plurality of passageways, channels or openings of the rigid ingrowth mesh is substantially 90°. It has been realized that it is extremely difficult for skin epithelium cells to pass over a squared edge, and as a consequence the growth of new tissue originating from the abdominal wall can be controlled and substantially limited to the interior section and possibly the anchoring flange. Consequently, squared laser cutting edges stops the skin epithelium cells growth inside the body.

The laser cutting technique are known to the skilled persons and further description can be found inter alia in the aforementioned international patent application no. PCT/IB2007/050646.

In a preferred embodiment the radial thickness of the interior section is smaller than the radial thickness of the exterior tubular section. This arrangement provides a thick exterior tubular section, which keeps the body duct substantially radially spaced apart from the circumference of the access opening. Furthermore, the reduced thickness of the interior section and the many through-openings of the implanted parts of the implant according to the present invention reduce the exposure of the body to large amounts of foreign implant materials.

BRIEF DESCRIPTION OF THE DRAWINGS

The implant according to the present invention is described below by way of examples in more details with reference to the accompanying drawing, in which.

DETAILED DESCRIPTION OF THE INVENTION

The invention is described below for use in an ostomy in which the body duct is an intestine. The skilled person would appreciate that the implant according to the present invention also can be used in other body accessing surgical procedure in which a vessel is externalised for creation of a stoma.

Figure 1:
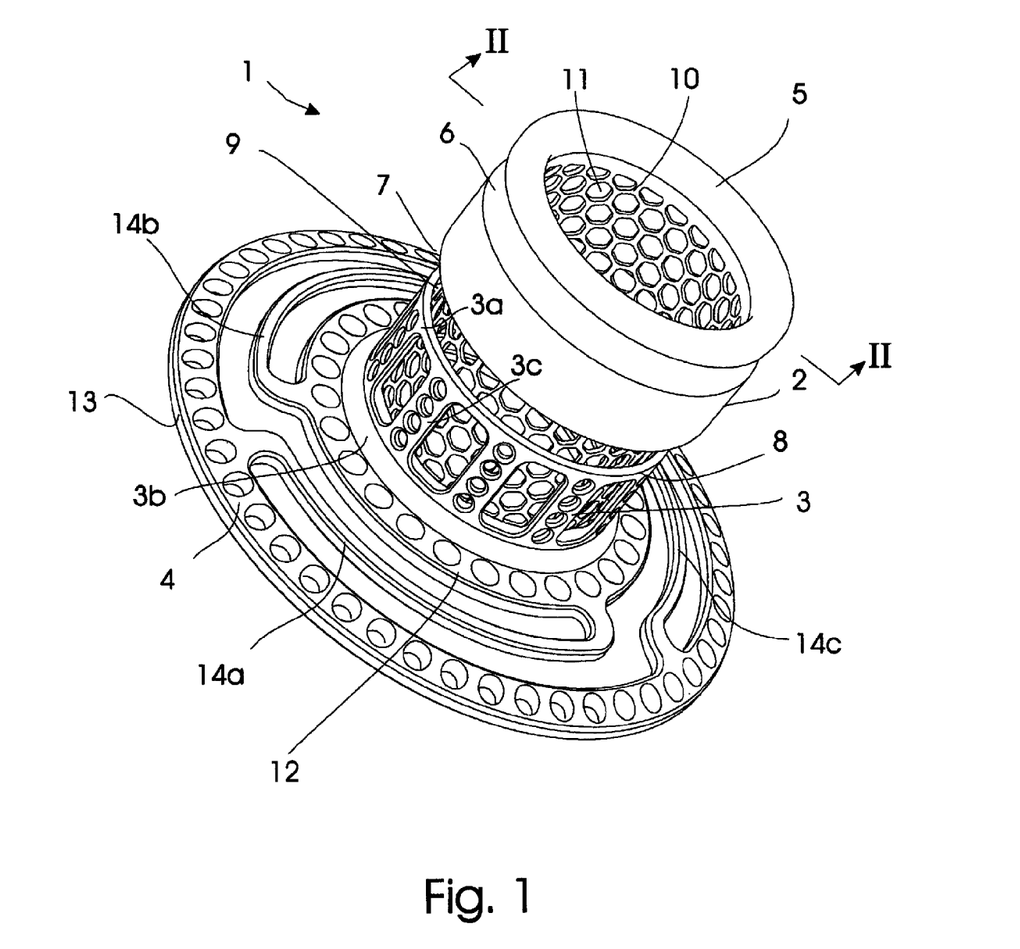
FIG. 1 shows a perspective view of a first embodiment of an implant according to the present invention.
Figure 2:
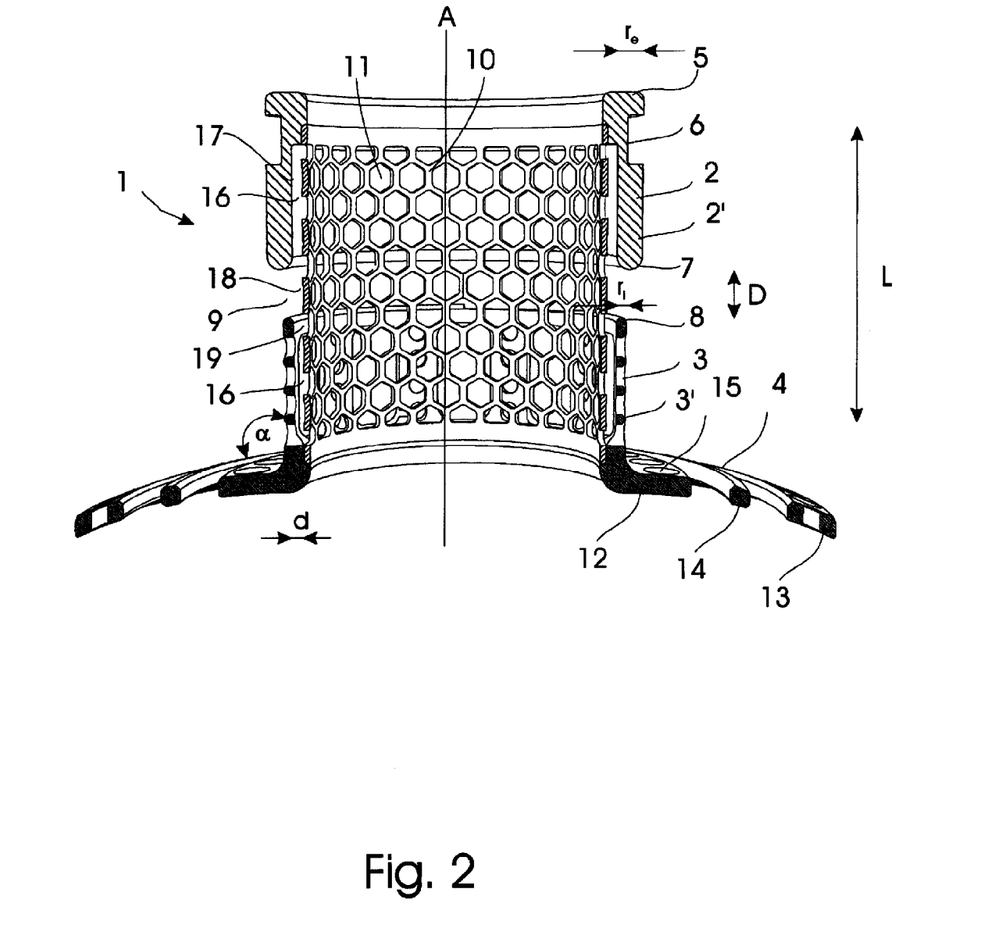
FIG. 2 shows a sectional view taken along line II-II of FIG. 1.

FIGS. 1 and 2 shows a first embodiment for a substantially tubular implant 1 consisting of an exterior tubular section 2 arranged spaced apart from an interior section 3, which extends radially into an anchoring flange 4 in an angle α of approximately 90°. The exterior tubular section 2 has a free end 5 provided with an annular mounting groove 6 for mounting of a detachable device, such as an ostomy bag. The free end 5 of the exterior tubular section has an opposing free end 7 facing towards a free end 8 of the interior section 3 opposite the anchoring flange 4.

The spaced apart relationship between the exterior tubular section 2 and the interior section 3 provides an open gap 9 delimited by the opposing free end 7 of the exterior tubular section 2 and the free end 8 of the interior section 3.

The exterior tubular section 2 and the interior section 3 are kept connected to each other by means of a rigid ingrowth mesh 10 having a plurality of laser cut hexagonal through openings 11.

The anchoring flange 4 consist of three concentric rings, a first ring 12, extending from the interior section 3 opposite the free end 8 of said interior ring 3. The first ring is connected to a concentric second ring 13 by means of connection members 14a,14b,14c, which may or may not be flexible. The connection members 14a,14b,14c connect the concentric rings 12,13 at offsets points. The flange 4 has in its entirety a slightly conical shape, i.e. the second ring is axial offset from the first ring away from the interior section. The flange also has a plurality of through-holes 15 for additional securing the implant inside the body. The specific design of the anchoring flange 4 shown in FIGS. 1 and 2 is described in further detail in the applicants own international patent application PCT/IB2007/050646. Other embodiments of anchoring flanges can be used within the scope of the present invention and the flange shown in the figures of the present application should not be seen as limiting.

The axial gap 9 between the exterior tubular section 2 and the interior section 3, which serves for closing the infection and inflammation route to the interior of the body is seen more clearly in the sectional view of FIG. 2. FIG. 2 also shows that the implant 1 has radial gaps 16 between the interior face 17 of the exterior tubular section 2 and the exterior face 18 of the rigid ingrowth mesh 10, and between the interior face 19 of the interior section 3 and the exterior face 18 of the rigid ingrowth mesh 10. The radial gap 15 serves for accommodation of new tissue, which infiltrate the rigid ingrowth mesh 10 via the through openings 11, and for the tissue bond between intestinal tissue and abdominal wall tissue at the interior section 3 implanted inside the body.

Figure 3:
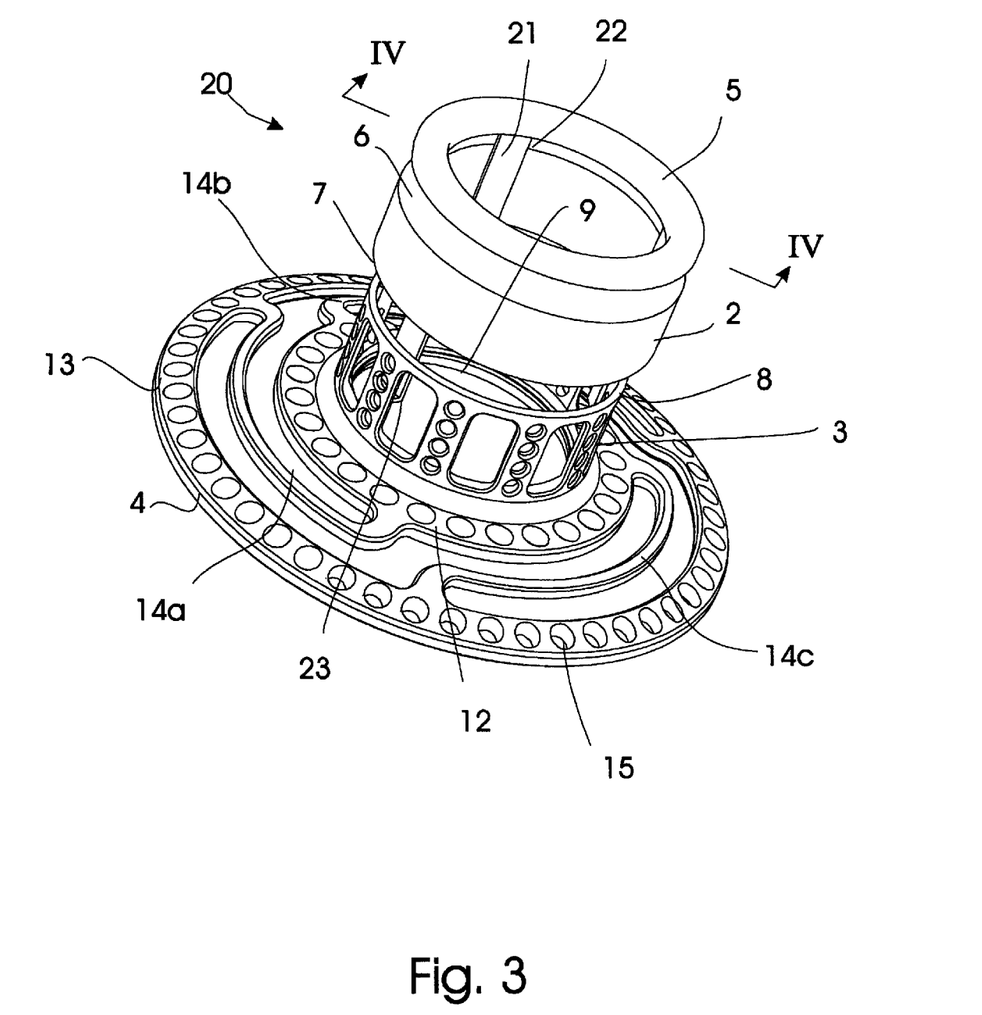
FIG. 3 shows a perspective view of a second embodiment of an implant according to the present invention.

The second embodiment for an implant 20 shown in FIG. 3 corresponds substantially to the first embodiment 1 shown in FIGS. 1 and 2 and for like parts same reference numerals are used.

The implant 20 only differs from the implant 1 in that the implementation of a different distance means. Instead of a rigid ingrowth mesh 10 three circumferential spaced apart rigid assembling members 21 are used as a distance means. Any other suitable number of assembling members may be chosen.

Figure 4:
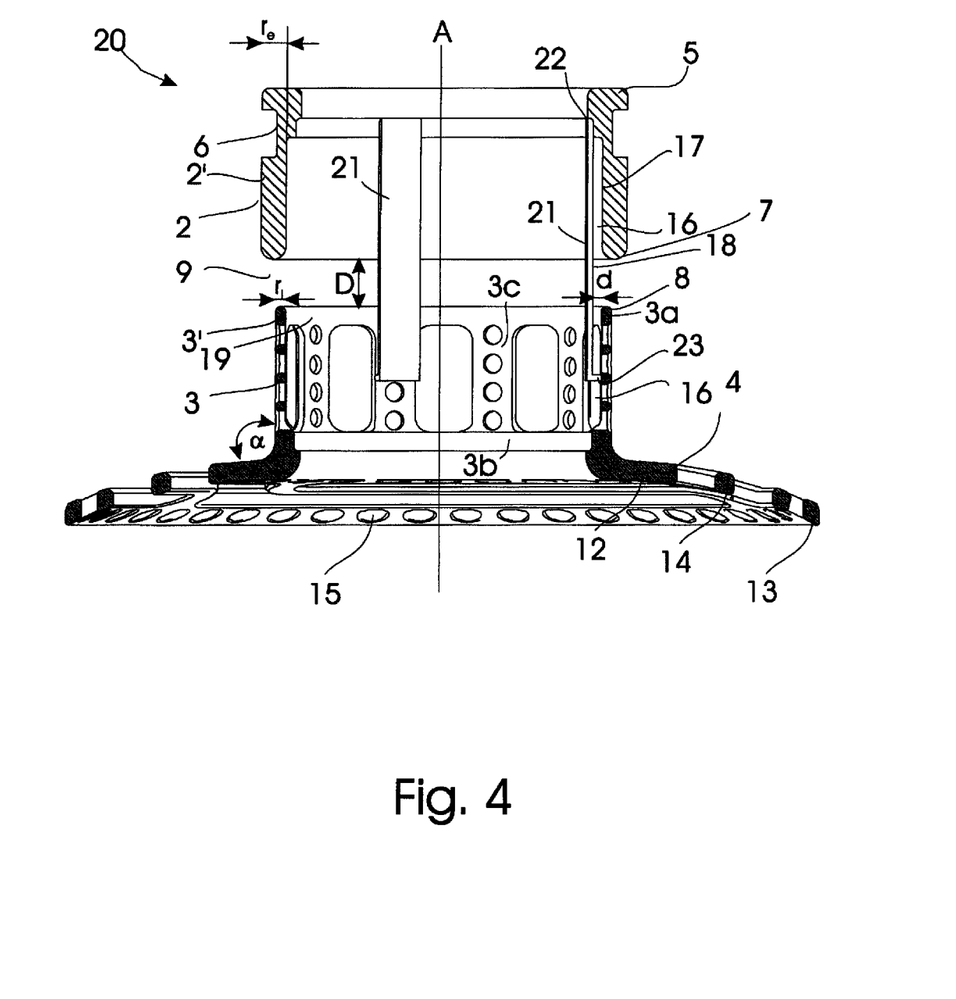
FIG. 4 shows a sectional view taken along line III-III of FIG. 3.

As seen best in the sectional view of FIG. 4 an assembling member may be shaped as an U-bend or L-bend bracket 21. One two brackets can be seen in FIG. 4. One end 22 of the L-bracket 21 is secured to the interior face 17 of the exterior section 3 and the other bend end 23 of the L-bend bracket 21 is secured to the interior face 19 of the interior section 2. In this manner the required radial gap 16 is obtained.

The implant 20 also has an axial gap 18 between the free end 7 of the exterior tubular section 2 and the free end 8 the interior tubular section 3. This embodiment is very open and is particular suitable for patients demonstration a high susceptibility to foreign implanted material.

The interior section 3 may for example be shaped as two concentric rings, a first ring 3a facing the exterior section 2 and a second ring 3b facing extending into the anchoring flange 4. The concentric rings 3a and 3b may be axially interconnected by e.g. a plurality of circumferential ribs 3c, crossbars or any other appropriate rigid latticework or netting.

The designs of a.o. the anchoring flange, the mounting groove and the ingrowth mesh may vary within the scope of the appended claims. Also, the length of the axial gap may be adapted to individual needs as well as the radial gap may be adjusted according to anatomic conditions. Examples of suitable designs of the interior section and anchoring flange are given in PCT/IB2007/050646.

The implant may be manufactured of any suitable biological acceptable material, preferably a material that can be laser cut.

What is claimed is:

1. A percutaneous implant for encircling and engaging an externalised length of a body duct of a human or animal patient, comprising:
    an exterior tubular section defined by an circumferential exterior wall at least a part of which is adapted to protrude outwardly from the abdominal wall with a free end which serves for mounting of a detachable device;
    an interior section adapted for internal fixation of the implant, with the interior section comprising a tubular member having a free end adjacent the free end of the exterior tubular section, and a radially extending anchoring flange for anchoring the implant inside the body,
    wherein the exterior tubular section and the interior section have a common axis A, with the exterior tubular section and the interior section arranged axially spaced apart from each other to provide an axial open gap that is parallel to the common axis A and that is delimited by the free end of the exterior tubular section and the free end of the tubular member,
    wherein the exterior tubular section and interior section are connected to each other by an ingrowth structure comprising a rigid ingrowth mesh or a plurality of rigid members, which mesh or plurality maintains the exterior tubular section and interior section spaced by the open gap and provides passageways, channels or openings that substantially or completely prevent formation of a biofilm between the exterior tubular and interior sections.

2. The percutaneous implant according to claim 1, wherein the rigid ingrowth mesh is shaped as a tubular body having a length L of at least the distance of the open gap between the exterior tubular section and the interior section.

3. The percutaneous implant according to claim 1, wherein the interior section includes a rigid ingrowth mesh for ingrowth of at least the exterior surface of the body duct wall along at least a part of the interior section.

4. The percutaneous implant according to claim 1, wherein the implant has a circumferential radial gap between the rigid ingrowth mesh or plurality of rigid members and the interior faces of either the exterior tubular section or the interior section or both.

5. The percutaneous implant according to claim 1, wherein the anchoring flange comprises a plurality of through-openings of the same or different sizes or combination of sizes.

6. The percutaneous implant according to claim 1, wherein the passageways, channels or openings of the rigid ingrowth mesh are of a polygonal cross-section.

7. The percutaneous implant according to claim 1, wherein the passageways, channels or openings of the rigid ingrowth mesh are of a hexagonal cross-section.

8. The percutaneous implant according to claim 1, wherein the plurality of passageways, channels or openings of the rigid ingrowth mesh have edges that are substantially 90° to the surface of the mesh.

9. The percutaneous implant according to claim 1, wherein the interior section has a radial thickness $r_x$, the exterior tubular section has radial thickness $r_e$ and radial thickness $r_x$ is smaller than radial thickness $r_e$.

10. The percutaneous implant according to claim 1 wherein the interior section is defined by an circumferential interior wall and the rigid ingrowth mesh extends inside the sections.

11. A combination of the percutaneous implant according to claim 1 with a detachable device mounted thereto.

12. The combination of claim 11, wherein the device is an ostomy bag.

13. A method of performing an ostomy procedure which comprises:
providing a percutaneous implant according to claim 1;
making an access opening through the abdominal wall of a patient;
locating the transcutaneous implant in the abdominal opening with the exterior section protruding from the patient and the interior section anchored inside the body; and
encircling and engaging an externalized length of a body duct with the implant.

14. The method of claim 13, which further comprises providing the interior faces of either of the exterior tubular section, the interior section or both with the rigid ingrowth mesh or plurality of rigid members for ingrowth of at least the exterior surface of the body duct therein.

15. The method of claim 13, which further comprises configuring the interior section as a radially extending anchoring flange for anchoring the implant inside the body, and providing the anchoring flange with a plurality of through-openings of the same or different sizes or combination of sizes.

16. The method of claim 15, wherein the openings of the anchoring flange are made by laser cutting.

17. The percutaneous implant according to claim 2, wherein the rigid ingrowth mesh serves at least for keeping the exterior tubular section and the interior section spaced apart in rigid relationship across the axial gap.

18. The percutaneous implant according to claim 1, wherein the anchoring flange extends from the end of the interior section opposite the free end of the tubular member.

19. A percutaneous implant for encircling and engaging an externalised length of a body duct of a human or animal patient, comprising:
an exterior tubular section defined by an circumferential exterior wall at least a part of which is adapted to protrude outwardly from the abdominal wall with a free end which serves for mounting of a detachable device;
an interior section adapted for internal fixation of the implant, with the interior section comprising a radially extending anchoring flange for anchoring the implant inside the body,
an interior section adapted for internal fixation of the implant, with the interior section comprising a tubular member having a free end adjacent the free end of the exterior tubular section, and a radially extending anchoring flange for anchoring the implant inside the body,
wherein the exterior tubular section and the interior section have a common axis A, with the exterior tubular section and the interior section arranged axially spaced apart from each other to provide an axial open gap that is parallel to the common axis A and that is delimited by the free end of the exterior tubular section and the free end of the tubular member,
wherein the exterior tubular section and interior section are connected to each other by a rigid ingrowth structure comprising circumferentially spaced ribs having a suitable length to keep opposing free ends of the exterior tubular section and the interior section spaced apart at a defined and permanent suitable distance corresponding to the open gap with the ribs sufficiently spaced apart to substantially or completely prevent formation of a biofilm between the exterior and interior sections.

20. A percutaneous implant for encircling and engaging an externalised length of a body duct of a human or animal patient, comprising:
an exterior tubular section defined by an circumferential exterior wall at least a part of which is adapted to protrude outwardly from the abdominal wall with a free end which serves for mounting of a detachable device;
an interior section adapted for internal fixation of the implant, with the interior section comprising a tubular member having a free end adjacent the free end of the exterior tubular section, and a radially extending anchoring flange for anchoring the implant inside the body,
wherein the exterior tubular section and the interior section have a common axis A, with the exterior tubular section and the interior section arranged axially spaced apart from each other to provide an axial open gap that is parallel to the common axis A and that is delimited by the free end of the exterior tubular section and the free end of the tubular member,
wherein the exterior tubular section and interior section are connected to each other by a rigid ingrowth structure comprising circumferentially spaced rigid connecting members that maintain the exterior tubular section and interior section spaced by the open gap with the connecting members being spaced apart or having sufficient openings to substantially or completely prevent formation of a biofilm between the exterior and interior sections.

21. The percutaneous implant according to claim 20, wherein the rigid connecting members comprise ribs, crossbars, latticework or netting.

\* \* \* \* \*

UNITED STATES PATENT AND TRADEMARK OFFICE
CERTIFICATE OF CORRECTION

| | | |
|---|---|---|
| PATENT NO. | : 8,821,462 B2 | Page 1 of 1 |
| APPLICATION NO. | : 12/674666 | |
| DATED | : September 2, 2014 | |
| INVENTOR(S) | : Axelsson et al. | |

It is certified that error appears in the above-identified patent and that said Letters Patent is hereby corrected as shown below:

<u>On the Title Page:</u>
Item (75) Inventors, after "Martin Johansson," change "Valda (SE)" to -- Vallda (SE) --.

Signed and Sealed this
Twenty-fifth Day of November, 2014

Michelle K. Lee
*Deputy Director of the United States Patent and Trademark Office*